(12) United States Patent
Nashed

(10) Patent No.: US 8,726,900 B1
(45) Date of Patent: May 20, 2014

(54) DEMAND ANESTHETIC GAS DELIVERY SYSTEM WITH DISPOSABLE BREATHING AND SCAVENGING CIRCUIT

(76) Inventor: Ramses Nashed, Tierra Verde, FL (US)

( * ) Notice: Subject to any disclaimer, the term of this patent is extended or adjusted under 35 U.S.C. 154(b) by 80 days.

(21) Appl. No.: 13/353,869

(22) Filed: Jan. 19, 2012

Related U.S. Application Data

(63) Continuation-in-part of application No. 12/658,019, filed on Feb. 1, 2010, and a continuation-in-part of application No. 12/800,626, filed on May 19, 2010, now Pat. No. 8,550,076.

(51) Int. Cl.
```
A61M 16/00    (2006.01)
A61M 16/10    (2006.01)
A61M 16/20    (2006.01)
A61M 16/01    (2006.01)
A61M 16/08    (2006.01)
```

(52) U.S. Cl.
USPC ............ 128/203.28; 128/203.12; 128/203.15; 128/203.25

(58) Field of Classification Search
CPC . A61M 16/00; A61M 16/0045; A61M 16/06; A61M 16/08; A61M 16/0816; A61M 16/0875; A61M 16/10; A61M 16/104; A61M 16/12; A61M 16/20; A61M 16/208; A61M 16/0087; A61M 16/009; A61M 2202/02; A61M 2202/0241; A61M 2016/00; A61M 2016/033; A61M 2016/0036; A61M 2016/0039; A61M 2016/0042; A61M 2016/0087; A61M 2016/009; A61M 2016/06; A61M 2016/08; A61M 2016/0816; A61M 2016/0866; A61M 2016/0883; A61M 2016/10; A61M 2016/208; A61M 2016/201; A61M 2016/20; A61M 2202/0208

USPC .......... 128/200.24, 203.12–203.17, 128/203.25–203.27, 204.18, 204.21, 128/205.24, 205.25, 205.26

See application file for complete search history.

(56) References Cited

U.S. PATENT DOCUMENTS

| | | | | | |
|---|---|---|---|---|---|
| 4,191,952 | A | * | 3/1980 | Schreiber et al. | 340/611 |
| 4,266,573 | A | * | 5/1981 | Braatz | 137/630.18 |
| 4,328,823 | A | * | 5/1982 | Schreiber | 137/88 |
| 4,527,558 | A | | 7/1985 | Hoenig | |
| 4,883,051 | A | * | 11/1989 | Westenskow et al. | 128/204.21 |
| 5,044,363 | A | * | 9/1991 | Burkhart | 128/205.27 |
| 5,099,834 | A | * | 3/1992 | Fishman | 128/203.12 |
| 5,228,434 | A | * | 7/1993 | Fishman | 128/203.12 |
| 5,404,873 | A | * | 4/1995 | Leagre et al. | 128/204.18 |
| 5,411,019 | A | * | 5/1995 | Smith | 128/203.25 |
| 5,676,133 | A | * | 10/1997 | Hickle et al. | 128/205.12 |
| 6,142,147 | A | * | 11/2000 | Head et al. | 128/204.21 |
| 6,273,087 | B1 | * | 8/2001 | Boussignac et al. | 128/204.22 |
| 7,455,062 | B2 | * | 11/2008 | Roehl et al. | 128/204.21 |
| 7,836,882 | B1 | * | 11/2010 | Rumph et al. | 128/203.12 |
| 7,900,633 | B2 | * | 3/2011 | Sinha | 128/207.14 |

\* cited by examiner

*Primary Examiner* — Annette Dixon
(74) *Attorney, Agent, or Firm* — Ronald E. Smith; Smith & Hopen, P.A.

(57) ABSTRACT

A demand valve is fixedly and rigidly mounted on an anesthetic gas mixer stand in close proximity to the gas mixer. A single-patient-use disposable breathing and scavenging circuit is adapted to be removably connected to the demand valve output for permitting a patient to breath gas, or a mixture gases, supplied by the gas mixer through a remotely located disposable face mask included as a portion of the breathing circuit. The breathing circuit further includes a scavenger portion for collecting exhaled waste gas from the face mask. The scavenger portion of the circuit also is disposable.

13 Claims, 4 Drawing Sheets

US 8,726,900 B1

DEMAND ANESTHETIC GAS DELIVERY SYSTEM WITH DISPOSABLE BREATHING AND SCAVENGING CIRCUIT

CROSS-REFERENCE TO RELATED APPLICATIONS

This nonprovisional application is a continuation-in-part of and claims priority to U.S. patent application Ser. No. 12/658,019, filed Feb. 1, 2010 by the same inventor, and is a continuation-in-part and claims priority to U.S. patent application Ser. No. 12/800,626, filed May 19, 2010 by the same inventor. Said prior applications are hereby incorporated hereinto by reference.

BACKGROUND OF THE INVENTION

1. Field of the Invention

This invention relates generally to devices for delivering anesthetic gas or gases in medical applications. More particularly, it relates to a novel respiratory gas delivery system of the "demand" or "self-administered" type adapted to be used with a disposable breathing and scavenging circuit.

2. Brief Description of the Related Art

The incorporated applications disclose novel respiratory face mask and breathing circuit assemblies adapted to be used with commercially available anesthetic gas handling equipment commonly and heretofore used in dentistry. Such anesthetic gas usually includes a mixture of nitrous oxide and oxygen. When employed as intended, the respiratory face mask and breathing circuit assemblies of the incorporated applications avoid contaminating the surrounding environment with built-up waste $N_2O$ gas, thereby facilitating safe and effective combined use of such equipment for sedation purposes in a hospital or other clinical environment as distinguished from a dentist's office.

U.S. Pat. No. 4,527,558 to Hoenig discloses a system for delivering anesthetic gas to a patient from a gas mixing device through a combined breathing mask and a demand valve assembly. A demand valve is normally closed to the flow of gas therethrough, but is responsive to the vacuum caused by a patient breathing through the mask attached to the valve, to allow the passage of gas through the valve and mask assembly until the patient ceases to inhale, or begins to exhale.

When the patient exhales, the demand valve has already shut off the supply of anesthetic gas until the next inspiration cycle. In the '558 patented system, the combined mask and demand valve assembly (i.e. both units) is located remotely and distally at the end of a flexible supply hose or tube which, in turn, is connected to the gas mixing device. This enables the patient to hold the demand valve and mask assembly by hand and self-administer the aesthetic gas (e.g. typically a mixture of $N_2O$ and oxygen). In the system of the '558 patent, a separate flexible tube attached to the output of the demand valve is connected to a surge tank or chamber for storing exhaled gas so as to ostensibly help prevent the exhaled gas from contaminating the room environment. The surge tank, in turn, is connected to a central vacuum system for scavenging the exhaled waste gas stored in the surge tank.

The disclosure of U.S. Pat. No. 4,527,558 is hereby incorporated hereinto and made part of this application by reference.

The foregoing anesthetic gas delivery and scavenging system according to the '558 patent has several disadvantages. Because the demand valve and mask assembly is held by the patient, and the patient breathes through the demand valve and scavenging (exhalation) tubing and surge tank, these fixed non-disposable components of the system must be cleaned or sterilized after each patient use to avoid cross-contamination (i.e. only the face mask or insert is disposable). Additionally, because the patient must manually grasp the relatively bulky mask and demand valve assembly during gas administration, the demand valve, a relatively delicate mechanism, is susceptible of being damaged by being dropped or otherwise mishandled by the patient. Moreover, the scavenger or surge tank is of fixed volume and can be overwhelmed by vigorous exhalation causing venting and possible room contamination. Also, the surge tank tends to collect moisture which compromises its function and tends to promote growth of bacteria or other contagions. Finally, the surge tank includes a hydrophobic polyurethane resistance plug which may increase the difficulty of exhalation experienced by the patient.

However, in view of the art considered as a whole at the time the present invention was made, it was not obvious to those of ordinary skill in the field of this invention how the shortcomings of the prior art could be overcome.

BRIEF SUMMARY OF THE INVENTION

To overcome the forgoing disadvantages and difficulties, the novel system provides a new and improved "demand" anesthetic gas delivery system including a gas mixing device preferably supported on an upright portable stand, and a demand valve fixedly and rigidly supported by a bracket or arm suitably mounted in a stationary fashion on the portable stand in close proximity to the mixing device.

A completely disposable breathing and scavenging circuit includes a flexible fresh gas supply tube, a face mask connected to the fresh gas supply tube, an exhalation tube connected to the face mask, a compliant flexible exhalation-reservoir bag connected to the exhalation tube via a one-way check valve, and a scavenging tube connected to a bottom opening provided in the reservoir bag. The distal end of the scavenging tube is adapted to be connected to a hospital central vacuum system or the like. The scavenging tube preferably also includes a vacuum compensator means for smoothly matching the relatively high vacuum flow rate of the central vacuum system to the lower end-tidal flow rate of a typical patient and thereby avoid collapse of the flexible reservoir bag.

In use, the fresh gas supply tube of the disposable circuit is connected to the output port of the demand valve which is located in a fixed, stationary manner on the portable gas mixer stand, and the distal end of the scavenging tube of the circuit is connected to the hospital central vacuum system.

The patient remotely holds only the face mask by hand which is connected to the other or distal end of the fresh gas supply tube. When the patient wishes to draw anesthetic gas from the mixer, he or she breathes (inspires) through the face mask and the fresh gas supply tube connected between the mask and the remotely located demand valve thereby opening the remotely located demand valve. The patient next exhales (demand valve "off") through the face mask and the breathing circuit's exhalation tube whereupon the exhaled waste gas flows through the one-way check valve into the compliant flexible reservoir bag.

The waste gas ultimately is drawn from the reservoir bag through the scavenger tube by the action of the central vacuum system connected thereto. When the patient is finished using the apparatus (i.e. after each single use), the entire breathing and scavenging circuit including the mask, the fresh gas supply tube, the exhalation tube, the one-way valve, the flexible reservoir bag, the vacuum compensator, and the scavenger tube are disconnected from the demand valve and central vacuum coupling, respectively, and disposed of as medical waste. The patient's waste or exhaled breath never comes into contact with the demand valve, and the patient only holds the face mask and the remote end of the fresh gas supply tube during each such single use.

The invention is not limited to the details of construction and to the arrangements of the components set forth in the following description or illustrated in the drawings. The invention includes additional embodiments and can be being practiced and carried out in various ways. The phraseology and terminology employed herein are for the purpose of description and should not be regarded as limiting.

An object of the invention to provide a novel demand anesthetic gas delivery system with a disposable breathing and scavenging circuit that has all of the advantages of the prior art and none of the disadvantages.

Another object is to provide a new and improved anesthetic gas delivery system with a disposable breathing and scavenging circuit that is especially suitable for use in administering anesthetic gas or gases to a patient on demand without causing any exhaled waste gas to build-up in the surrounding environment.

Another object is to provide a novel demand anesthetic gas delivery system wherein a gas mixer is supported on a portable stand, a demand valve is attached to the portable stand in a fixed, stationary manner proximal to the gas mixer, and an entirely disposable breathing circuit including a breathing or face mask, fresh gas supply tube, exhalation tube, compliant flexible exhalation reservoir bag and scavenging circuit is provided such that a patient is adapted to breath and exhale through the mask and the breathing circuit by manually holding only the mask or the fresh gas supply tube, or both.

A further object is to provide a novel demand anesthetic gas delivery system wherein a gas mixer is supported on a portable stand, a demand valve is attached to the portable stand in a fixed, stationary manner proximal to the gas mixer, and a completely disposable breathing circuit including a breathing or face mask, fresh gas supply tube, exhalation tube, compliant flexible exhalation reservoir bag and scavenging circuit is provided such that the face mask is adapted to be connected to the remotely located demand valve through the fresh gas supply tube, and the same face mask is adapted to be connected to a hospital central vacuum system or the like via the exhalation tube, the compliant flexible reservoir bag and the scavenging circuit.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which are illustrated preferred embodiments of the present invention.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

With reference initially to FIGS. 1-4 of the drawings, a first preferred embodiment of the novel demand anesthetic gas delivery system with disposable breathing and scavenging circuit according to the invention will now be described in detail.

Figure 1:
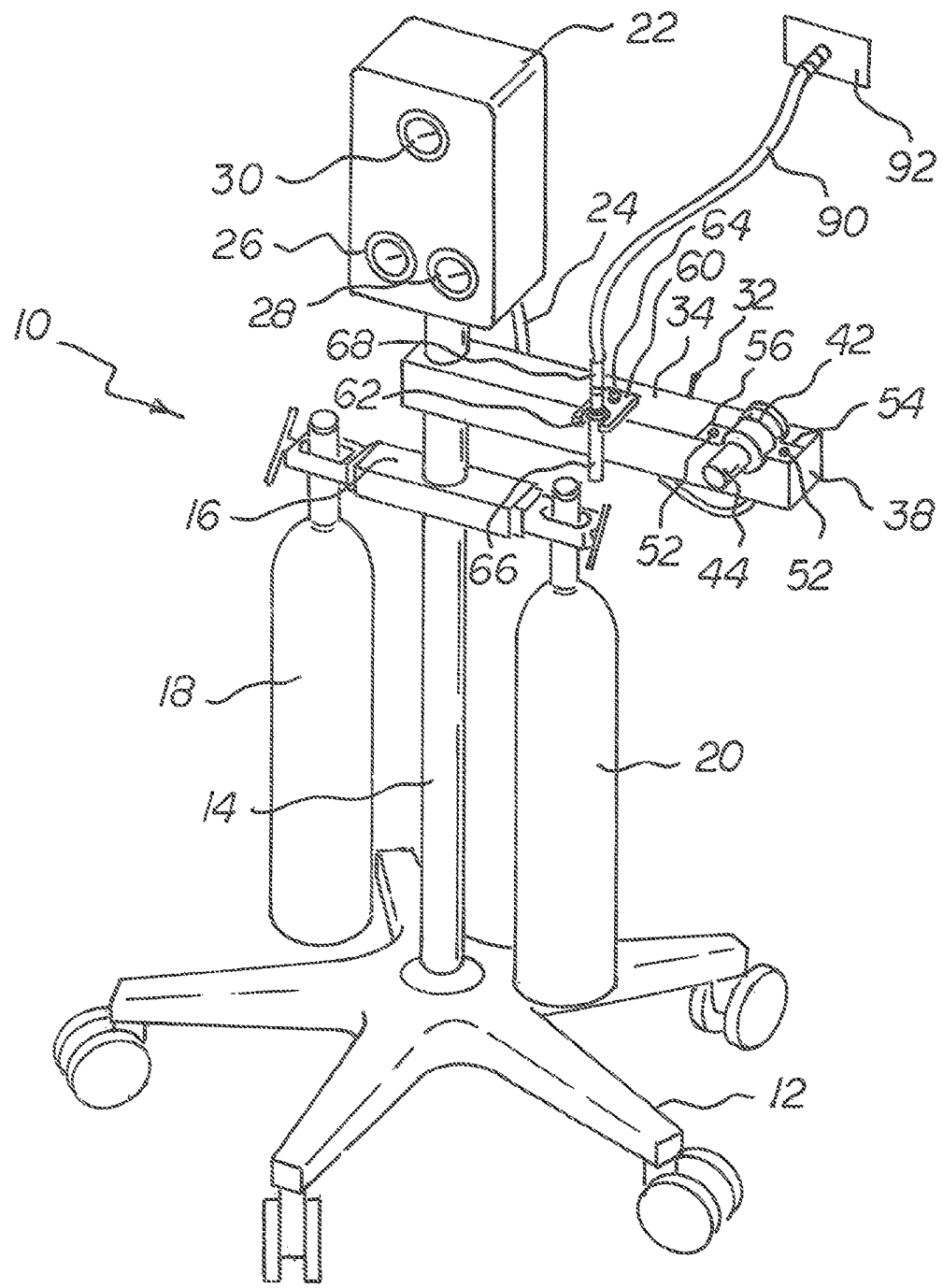
FIG. 1 is a perspective view depicting the novel anesthetic gas mixing device and demand valve mounted on a portable stand.

As depicted in FIG. 1, a portable stand generally represented by reference sign 10 includes a wheeled base or dolly 12, and an upright post or riser 14 fixedly supported centrally on dolly 12. Suitably fixed to riser 14 is a transverse pressurized-gas container bracket 16 for supporting substantially as depicted a first pressurized gas container or cylinder 18 of nitrous oxide ($N_2O$) and a second pressurized gas container or cylinder 20 of oxygen ($O_2$). Bracket 16 is conventional and includes clamping collars and valves of well-known construction for securely supporting each pressurized-gas cylinder and permitting gas from each cylinder to flow into the interior of a gas mixer 22 through suitable hose connections (not shown) upon selective opening of a suitable valve (not labeled) on top of each cylinder 18, 20, respectively, as is well known in the medical art.

Fixedly mounted on top of riser 14 is the aforementioned gas mixer 22 of known construction which is adapted to receive the gases from cylinders 18, 20, through suitable hoses (not shown) connected between bracket 16 and mixer 22, combine them to form a gas mixture, and thence make available a continuous supply of the gas mixture through a flexible gas supply hose or tubing 24. Gas mixer 22 can be one of several such devices commercially available. One such known device, preferred in practicing the present invention, is manufactured by Fraser Harlake and sold under the trademark NITRONOX.

As schematically depicted, the front panel of the NITRONOX® gas mixer 22 includes gauges 26, 28, 30 for displaying the nitrous supply pressure, the oxygen supply pressure, and the gas mixture supply pressure made available through supply hose 24, respectively. The construction of the NITRONOX® device is conventional.

Thus far, the apparatus described essentially is similar to that disclosed in U.S. Pat. No. 4,527,558. However, in the latter patented device, the supply hose connected to the output of the mixer is of substantial longitudinal extent (e.g. about 52 inches) and terminates in a combined demand valve and face mask assembly adapted to be held or manually grasped by a patient remotely with respect to the gas mixer.

Figure 2:
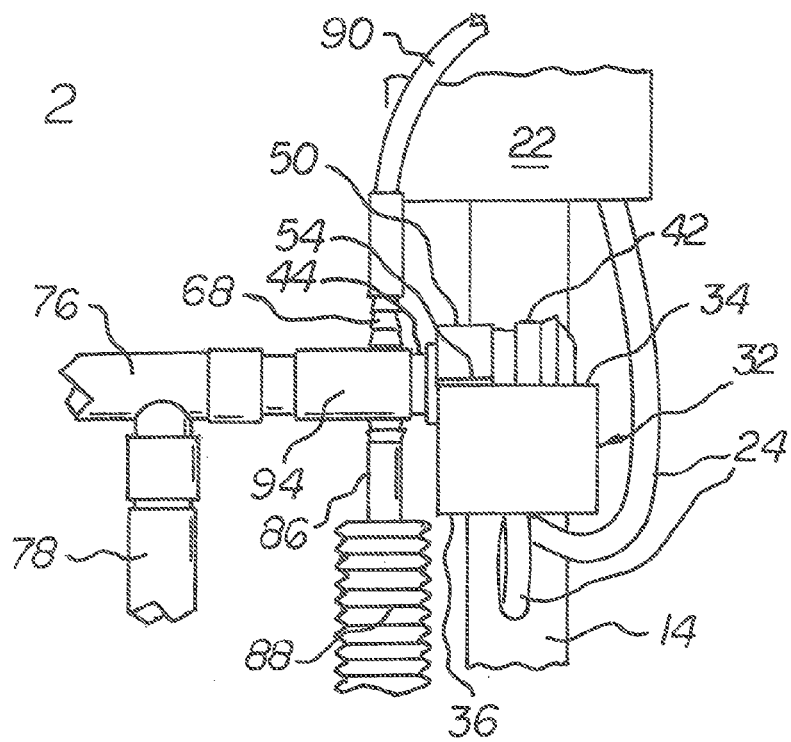
FIG. 2 is an enlarged side view in elevation of a portion of FIG. 1 depicting mounting of the demand valve on its support arm or bracket.
Figure 3:
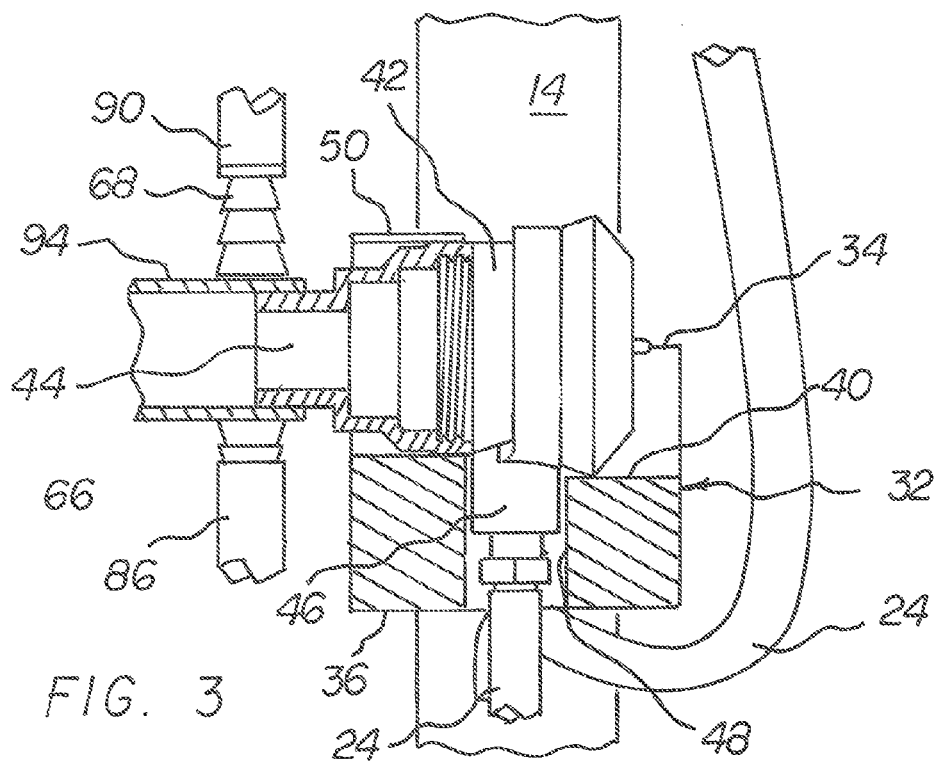
FIG. 3 is an enlarged cross-sectional view taken along line 3-3 in FIG. 2.

In contrast, in the present invention, the demand valve is entirely separate from any face mask and is fixedly supported directly on stand 10 proximal to the mixer 22. Hence, as depicted in FIGS. 1-3, a transverse bracket or arm 32 is fixedly attached to riser 14 and includes a top surface 34, a bottom surface 36, and an end face 38. Proximal to end face 38, arm top surface 34 has a transverse semi-circular groove 40 recessed therein providing a seat or pocket for receiving the bottom portion of generally cylindrically-shaped demand valve 42 substantially as shown. Demand valve support arm 32 can be rigidly and fixedly secured to riser post using the same or similar set-screw and clamping bracket (not shown) used to secure bracket 16 to riser 14, such hardware being well known.

Turning to FIGS. 2 and 3, demand valve 42 includes output nozzle 44 facing forwardly or to the left as depicted in FIGS. 2 and 3, and further includes input nozzle 46 facing downwardly as viewed in FIG. 3 with input nozzle 46 being received in a through-passage 48 provided in arm 32 and extending upwardly from bottom surface 36 of arm 32 to intercept the bottom of groove 40 (FIG. 3). As further depicted in FIG. 3, the distal end of flexible gas supply hose 24 extends into through-passage 48 whereupon it is suitably securely connected to demand valve input nozzle 46.

As will be made more evident below, in accordance with the present invention, the fresh gas input end of a disposable breathing and scavenging circuit is adapted to be removably connected to output nozzle 44 of demand valve 42. A generally C-shaped clamping bracket 50 can be employed to fixedly and rigidly secure demand valve 42 in groove 40 (and therefore on arm 32) by means of threaded screw fasteners 52 or the like extending through end tabs 54, 56 provided on opposite ends of clamping bracket 50 and being received in complimentary threaded holes (not labeled) suitably provided in arm top surface 34. By such means, the screw fasteners may be loosened and clamping bracket 50 removed to permit easy repair, cleaning or replacement of demand valve 42.

Due to the proximal fixed location of demand valve 42 relative to gas mixer 22 on bracket or arm 32, a relatively short length of supply hose 24 is required to connect the mixer to the input nozzle of the demand valve. For the sake of neatness, the relatively short-length supply hose 24 can be trained to the underside of arm 32 by means of spring clips or the like (not shown). Demand valve 42 is a known commercial item and is readily available from medical supply firms.

Preferably, stand-off bracket 60 for supporting flow-through adaptor 62 in a vertical orientation is fastened to top surface 34 of arm 32 by means of screw fastener 64 or the like threadedly received in a complimentary threaded hole (not labeled) in top surface 34 substantially as shown. Flow-through adaptor 62 includes bottom nozzle or nipple 66 adapted to be connected to the distal end of the scavenging limb of a breathing circuit as will made more apparent below. Flow-through adaptor 62 also has a top nozzle or nipple 68 adapted to be connected to a conventional vacuum hose for ultimate connection to the wall outlet of a hospital central vacuum system or the like (FIG. 4).

Figure 4:
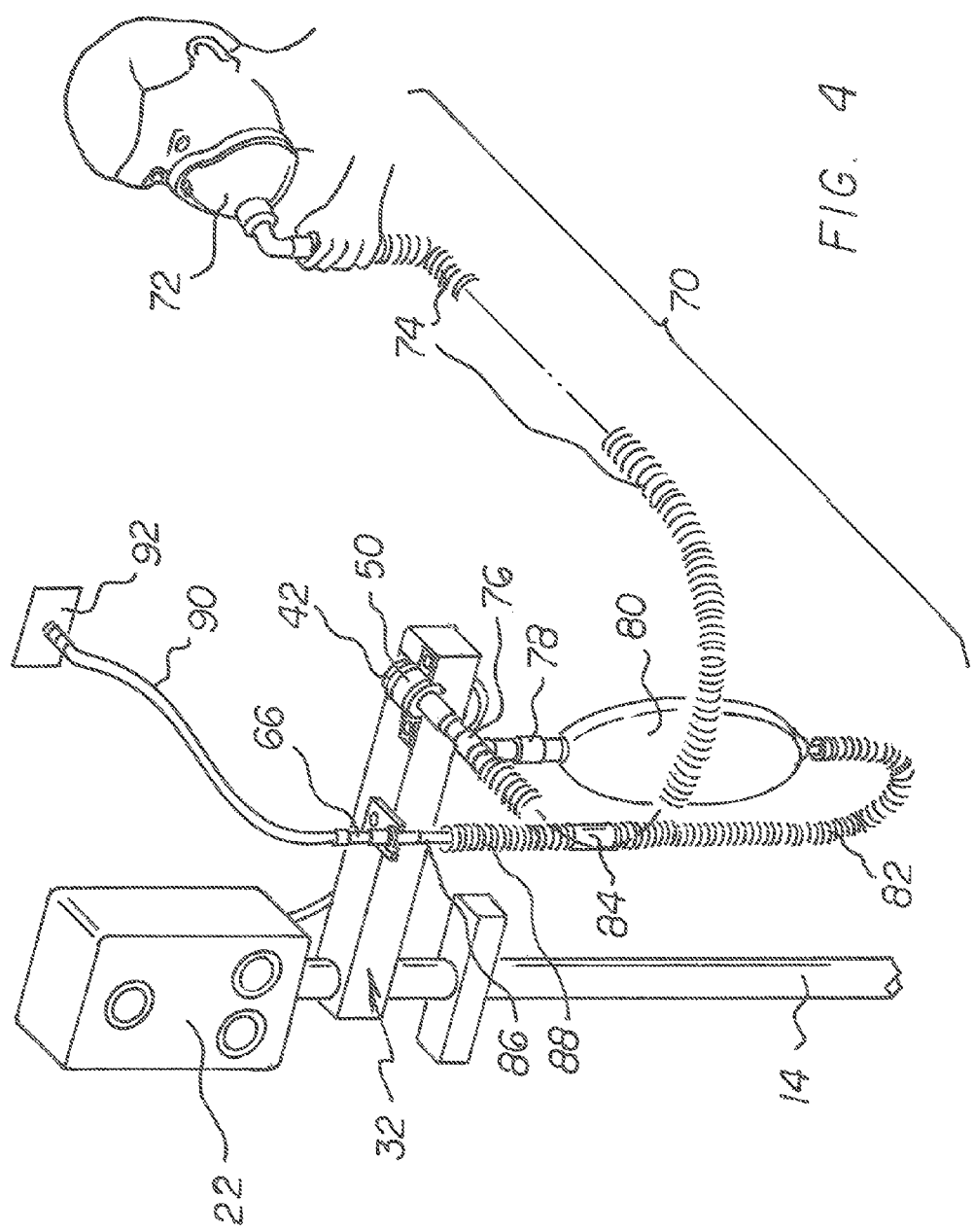
FIG. 4 is a schematic assembly view depicting a first alternatively preferred embodiment of the disposable breathing circuit and scavenging circuit connected to the portable stand of FIG. 1 and further schematically depicting self-administration of anesthetic gas to and by a patient in accordance with the invention.

In accordance with the present invention, and referring to FIGS. 2-4, the apparatus 10 of FIG. 1 can be used with an entirely disposable single-use breathing and scavenging circuit generally represented by reference sign 70. The preferred disposable breathing and scavenging circuit 70 is disclosed in co-pending U.S. application Ser. No. 12/658,019; filed Feb. 1, 2010.

The disposable single-use breathing and scavenging circuit 70 depicted in FIGS. 2-4 includes face mask 72 connected to a suitable length of co-axial flexible tubing 74 connected proximally at one end to face mask 72. As schematically indicated in FIG. 4, face mask 72 is adapted to be sealing fitted to a patient's face sufficient to cover at least the nose and mouth of the patient preferably by having the patient hold the mask in the desired position substantially as schematically shown in FIG. 4. Face mask 72 preferably is of the type that not only covers the nose and mouth of the patient, but furthermore engages underneath the patient's chin. Such anesthesia face masks and the advantages of using them are fully disclosed in the incorporated patent applications.

The other or opposed end of co-axial flexible tubing 74 is distally connected to a branched coupling or T-coupling 76. The co-axial flexible tubing 74 includes an inner tube or passageway for conveying fresh gas and a co-axial outer tube or passageway for conveying exhaled waste gas between mask 72 and branched or T-coupling 76. By such arrangement, fresh or inspired gas is adapted to enter one leg or branch of T-coupling 76, flow through the inner passageway in co-axial flexible tubing 74 and enter the interior of mask 72. Similarly, exhaled waste gas is adapted to flow from the interior of mask 72 into and through the outer passageway in flexible tubing 74 and exit through the second leg or branch of T-coupling 76.

Disposable circuit 70 further includes one-way check valve 78 connected at its input end to the second or exhalation output leg of T-coupling 76 and which is connected at its output end to the top of a flexible, compliant flow-through reservoir bag 80 having suitable openings (not shown) in its top end and bottom end, respectively. The output or bottom end of flexible bag 80 is connected to one end of a suitable length of single-lumen flexible transition tubing 82 (J-shape tubing, FIG. 4), the other end of which is distally connected to the scavenging tube or limb portion of circuit 70.

The scavenging portion includes a vacuum mitigation means or compensator 84, a first length of flexible tubing 86 connected at its proximal end to compensator 84, and a second length or sleeve of flexible tubing 88 connected to compensator 84 at its proximal end and co-axially oriented with respect to the first length of tubing 86.

Sleeve 88 has a length less than that of tubing 86 and has a diameter greater than that of tubing 86. The distal end of sleeve 88 is open thereby providing an annular opening through which room air may be drawn into compensator 84 under the influence of a vacuum present in tubing 86, the purpose of which is to reduce the relatively high vacuum imposed upon the flexible reservoir bag through transition tubing 82, vacuum compensator 84, and first length of tubing 86 by the central vacuum system of a hospital or similar clinical environment.

In operation, the gas supply apparatus 10 of FIG. 1 is wheeled into proximity of a patient and conventional flexible vacuum hose 90 is employed to connect the upwardly extending nipple 68 of flow-through adaptor 62 to the wall outlet 92 of a hospital central vacuum system or the like. Disposable breathing circuit 70 then is removed from its factory wrapper and one end of coaxial tube 74 attached to face mask 72 in a known manner. The other end of coaxial tube 74, namely T-coupling 76 is then sealing slidingly fitted, preferably through a stand-off or extension bushing 94, to output nozzle 44 of demand valve 42 (FIGS. 2 and 3). Then, to complete the hook-up of circuit 72 with the gas apparatus 10, the distal extremity or end of tubing 86 of the scavenger portion of circuit 72 is sealing slidingly fitted onto downward depending nipple 66 of flow-through adaptor 62 (FIG. 2).

The respective valves on the top of the nitrous oxide and oxygen containers may then be opened to supply a mixture of these gases to input 46 of demand valve 42. The patient is now ready to lift the mask to his or her face in a sealing and comfortable manner and to inhale therethrough. Such inhalation is effective to create a negative pressure in the fresh gas supply passageway of coaxial tube 74 sufficient to cause demand valve 42 to open, allowing inspiration of the fresh gas mixture through the flexible tube 74 and face mask 72.

When the patient exhales, the demand valve closes and the exhaled waste gas flows through the exhalation passageway of tube 74, the second leg of branch or T-coupling 76, the one-way valve 78, and thence into compliant flexible reservoir bag 80 causing the bag to expand slightly to accommodate the exhaled waste gas. The vacuum present in tubing 86 draws the waste gas through the opening in the bottom of bag 80, through compensator 84, through tubing 86, out through nipples 64, 66 of adaptor 62, through vacuum hose 90 and finally into the central vacuum system of the hospital or the like.

Collapse of flexible reservoir bag 80 by the relatively high vacuum present in the central vacuum system is avoided by the action of room air flowing through the open distal end of sleeve 88.

Following inspiration, the patient can retain mask 72 fitted on his or her face and engage in another breathing cycle of mixed gas supplied from gas mixer 22 through demand valve, or the patient may place the mask down away from the face of the purpose of temporarily resting and breathing room air. It is thus seen that the unique demand system of the present invention is advantageously suited for self-administration of anesthetic gas, directly by the patient under only minimal supervision by a care provider. Obviously, it will be appreciated that face mask 72 and coaxial tubing 74 optionally may be held directly on the patient's face by a care provider if such assisted administration is necessary or desired instead.

Once the patient's medical procedure is completed, circuit 70 may be removed from gas apparatus 10 merely by removing T-coupling 74 from output nozzle 44 of demand valve 42; then removing the distal end of tube 86 from nipple 64 of flow-through adaptor 62. The entire circuit including face mask 72 then may be disposed of as medical waste.

Figure 5:
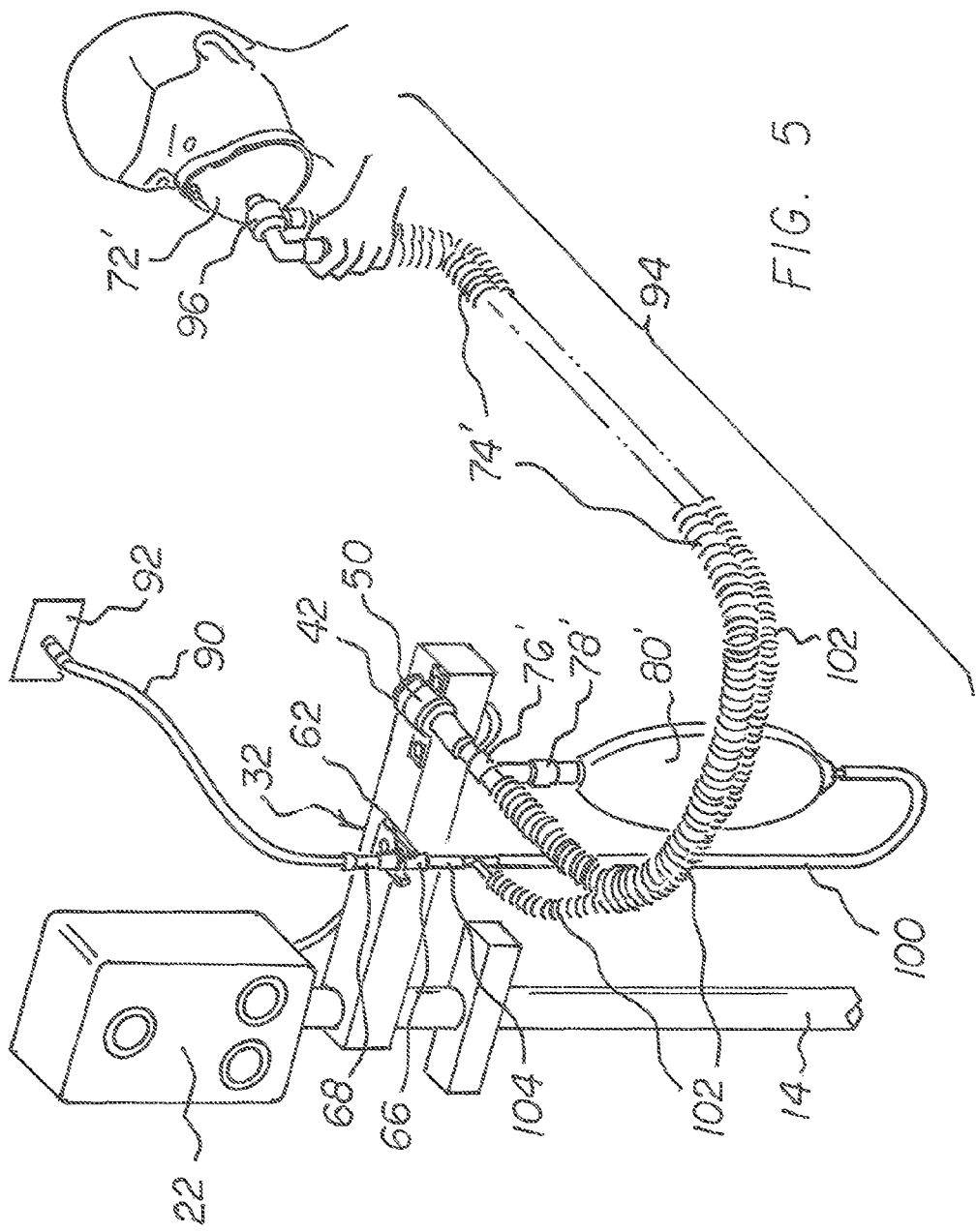
FIG. 5 is a schematic assembly view showing an alternatively preferred embodiment of the disposable breathing and scavenging circuit connected to the portable stand of FIG. 1 and further schematically depicting the self-administration of anesthetic gas to and by a patient in accordance with the invention.

Turning now to the alternatively preferred embodiment of the present invention depicted in FIG. 5, a somewhat different disposable breathing and scavenging circuit generally represented by reference numeral 94 is optionally employed with gas apparatus 10 of FIG. 1.

Circuit 94 can be the same as that disclosed in the incorporated disclosures.

With reference to the present invention and as depicted in FIG. 5, alternatively preferred circuit 94 includes face mask 72' connected to a suitable length of co-axial flexible tubing 74' connected proximally at one end to face mask 72'. The other or opposed end of co-axial flexible tubing 74' is distally connected to branched coupling or T-coupling 76'. As in the prior embodiment of FIGS. 2-4, the co-axial flexible tubing 74' includes an inner tube or passageway for conveying fresh gas and a co-axial outer tube or passageway for conveying exhaled waste gas between mask 72' and branched or T-coupling 76'. Circuit 94 also includes one-way valve 78' and flexible reservoir bag 80' connected serially to the output leg of branched coupling 76'.

However, in lieu of the length of single-lumen flexible transition tubing 82 (J-shape tubing, FIG. 4) and the scavenging portion including vacuum compensator 84, the first length of flexible tubing 86 connected at its proximal end to compensator 84, and the second length or sleeve of flexible tubing 88 connected to compensator 84 at its proximal end co-axially oriented therewith, the alternatively preferred embodiment of FIG. 5 includes an annular suction collar 96 suitably mounted proximal to the junction between the flexible tube 74' and face mask 72', a Y-connector 98 which functions as a vacuum divider or splitter, a first length of smooth tubing 100 connected between a first branch of Y-connector 98 and the bottom opening in bag 80', a second length of corrugated tubing 102 connected between the annular suction collar 96 and a second branch of Y-connector 98, and a third length of smooth tubing 104 connected proximally at one end thereof to a third branch of the Y-connector 98.

As depicted in FIG. 5, the opposed or distal end of the third length of smooth tubing 104 is adapted to be connected slidingly and sealing to downwardly depending nipple 64 on adaptor 62 for ultimately connecting Y-connector 98 to a source of vacuum through upper nipple 66 and flexible vacuum hose 90. The scavenger portion of alternatively preferred circuit 94 comprises the annular suction collar 96, the Y-connector 98, the first length of smooth tubing 100 connected between the Y-connector 98 and the bottom opening in bag 80', the second length of corrugated tubing 102 connected between the annular suction collar 96 and Y-connector 98, and the third length of smooth tubing 104 connected between nipple 64 of flow-through adaptor 62 and Y-connector 98. As in the prior embodiment, these parts making up the scavenging portion of circuit 94 function as the gas compensator to divide the relatively high vacuum present in the central vacuum system into a first lesser vacuum drawing on the bottom opening of flexible reservoir bag 80' and a second lesser vacuum drawing on the annular opening of suction collar 96 proximal to the apex of face mask 72' all as more fully set forth in the incorporated disclosures.

Notwithstanding the foregoing differences, in operation, the alternatively preferred disposable breathing and scavenging circuit 94 of FIG. 5 is used and performs substantially in the same manner as circuit 70 of FIGS. 2-4.

The face mask, breathing circuit and scavenging circuit components are disposable and intended for a single-patient-use to avoid cross-contamination. In this regard, the respiratory face mask, breathing circuit and scavenging circuit components of the present invention can be made from inexpensive and durable plastic or metal materials. The disposable breathing and scavenging circuit embodiments of the present invention including the disposable face mask employed therewith may be packaged together as a convenient unitary kit, or provided in separate packages, respectively.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

What is claimed is:

1. An apparatus for supplying an anesthetic gas, or mixture of gases to a patient on demand, comprising:
   a gas mixer mounted on a stand;
   a demand valve;
   a hose providing fluid communication between said gas mixer and said demand valve;
   a disposable face mask in fluid communication with said demand valve;
   a support connected to said stand proximal to said gas mixer, said demand valve being securely mounted on said support in a stationary location relative to and proximal to said gas mixer;
   a disposable breathing and scavenging circuit, said breathing and scavenging circuit providing fluid communication between said disposable face mask and said demand valve such that said disposable face masks and said patient are situated remotely with respect both to said gas mixer and said demand valve;

said disposable breathing and scavenging circuit including a first and a second length of flexible tubing, said first length nested in a lumen of said second length so that said first and second lengths collectively form a flexible, coaxial tubing;

a gas coupling having first and second branches, said first branch having a first end and a second end and said second branch having a first end and a second end;

said second end of said first branch of said gas coupling in fluid communication with said demand valve;

said first end of said first branch of said gas coupling in fluid communication with a second end of said first length of flexible tubing;

a first end of said first length of flexible tubing in fluid communication with said disposable face mask;

a flexible compliant reservoir bag having a top, entry opening and a bottom, exit opening so that it is a flow-through bag;

said first end of said second branch of said gas coupling in fluid communication with a second end of said second length of flexible tubing;

said second end of said second branch of said gas coupling in fluid communication with the top, entry opening of said flexible compliant reservoir bag;

a first end of said second length of flexible tubing in fluid communication with said disposable face mask;

a scavenging tube connected to said bottom, exit opening of said flexible compliant reservoir bag; and said scavenging tube adapted to provide fluid communication between said flexible compliant reservoir bag and a remote source of vacuum.

2. The apparatus of claim 1, further comprising:
a valve in fluid communication with said scavenging tube to cause room air to enter and flow through said scavenger tube in response to a vacuum applied to said scavenging tube.

3. The apparatus of claim 1, further comprising:
a disposable one-way check valve disposed between said second branch of said gas coupling and said top, entry end of said flexible compliant reservoir bag to prevent re-breathing of waste gas stored in said flexible compliant reservoir bag.

4. The apparatus of claim 1, further comprising:
said disposable face mask adapted to cover a nose and mouth of a patient and adapted to engage the underside of the patient's chin when said face mask is fitted on said patient's face.

5. The apparatus of claim 1, further comprising:
said stand being mounted on a wheeled dolly.

6. The apparatus of claim 1, further comprising:
said stand including a bracket for supporting first and second containers of gas on said stand.

7. The apparatus of claim 6, further comprising:
said first container containing nitrous oxide and said second container containing oxygen.

8. The apparatus of claim 1, further comprising:
said first branch of said gas coupling removably connected to the output of said demand valve.

9. The apparatus of claim 1, further comprising:
said support connected to said stand including an arm extending laterally from said stand; and
said demand valve secured to a distal free end of said arm.

10. The apparatus of claim 9, further comprising:
a scavenger coupling on said arm, said scavenger coupling having a first input end and a second output end;
said scavenging tube connected to said bottom, exit opening of said flexible reservoir bag adapted for fluid communication with said first input end of said scavenger coupling, and said second output end of said scavenger coupling adapted for fluid communication with said remote source of vacuum.

11. The apparatus of claim 10, further comprising:
said scavenger coupling mounted on said arm between said demand valve and said stand.

12. The apparatus of claim 9, further comprising:
a clamp for securing said demand valve to said arm.

13. The apparatus of claim 12, further comprising:
said clamp being removably mounted to enable servicing or replacement of said demand valve.

\* \* \* \* \*